(12) United States Patent
Segman

(10) Patent No.: US 10,736,550 B2
(45) Date of Patent: Aug. 11, 2020

(54) APPARATUS AND METHOD OF GENERATING PH OF SUBJECT FROM AT LEAST THREE WAVELENGTHS

(71) Applicant: CNOGA MEDICAL LTD., Or Akiva (IL)

(72) Inventor: Yosef Segman, Or Akiva (IL)

(73) Assignee: Cnoga Medical Ltd., Caesarea (IL)

( * ) Notice: Subject to any disclaimer, the term of this patent is extended or adjusted under 35 U.S.C. 154(b) by 287 days.

(21) Appl. No.: 15/610,654

(22) Filed: Jun. 1, 2017

(65) Prior Publication Data

US 2018/0344226 A1 Dec. 6, 2018

(51) Int. Cl.
*A61B 5/145* (2006.01)
*A61B 5/1455* (2006.01)
*A61B 5/00* (2006.01)

(52) U.S. Cl.
CPC ........ *A61B 5/14539* (2013.01); *A61B 5/1455* (2013.01); *A61B 5/7225* (2013.01); *A61B 5/7253* (2013.01); *A61B 5/7278* (2013.01); *A61B 5/6826* (2013.01); *A61B 2560/0228* (2013.01); *A61B 2560/0238* (2013.01); *A61B 2562/0233* (2013.01); *A61B 2576/00* (2013.01)

(58) Field of Classification Search
CPC .... A61B 5/1455–1464; A61B 5/14539; A61B 5/0059; A61B 5/7271; G01N 21/80; G01N 21/00
See application file for complete search history.

(56) References Cited

U.S. PATENT DOCUMENTS 5,039,492 A * 8/1991 Saaski .................... G01N 21/77
356/412
5,813,403 A * 9/1998 Soller .................. A61B 5/0075
600/310

(Continued)

OTHER PUBLICATIONS

Schreml, Stephan, et al. "A sprayable luminescent pH sensor and its use for wound imaging in vivo". Accepted for publication Sep. 26, 2012 in Experimental dermatology, Dec. 2012;21(12):951-3. doi: 10.1111/exd.12042.

(Continued)

*Primary Examiner* — Devin B Henson
*Assistant Examiner* — H. Q. Nguyen
(74) *Attorney, Agent, or Firm* — Mark M. Friedman

(57) ABSTRACT

An apparatus obtaining a pH level of a tissue comprises an array of at least three optical sensors configured to absorb light shined on the tissue and thereby obtain at least three electronic digital signals, wherein the first electronic signal $A_1(X,t)$ represents the light absorbed by the tissue in location $X=(X,Y,Z)$ at time t and at wavelength $L_1$, and similarly the second and third electronic signal $A_2(X,t)$ and $A_3(X,t)$, and a finite absorption range of the three wavelength $L_1$, L2 and $L_3$ is such that $0<=A_3(X,t)<=A_2(X,t)<A_1(X,t)$; and an electronic processing unit receives the signals and applies an ordered monotone function, F1, to the tissue, to spatial temporal information of each wavelength, F1 used by a transfer function for presentation as a LookUp Table connecting actual values computed by F1 and an actual pH of the tissue in location X at time t.

18 Claims, 6 Drawing Sheets

(56) References Cited

U.S. PATENT DOCUMENTS

| | | | |
|---|---|---|---|
| 7,043,293 B1* | 5/2006 | Baura | A61B 5/04017 |
| | | | 600/509 |
| 7,198,756 B2 | 4/2007 | Kimball et al. | |
| 8,335,550 B2* | 12/2012 | Segman | A61B 5/0059 |
| | | | 356/300 |
| 2006/0253007 A1 | 11/2006 | Cheng et al. | |
| 2009/0299154 A1* | 12/2009 | Segman | A61B 5/0059 |
| | | | 600/301 |

OTHER PUBLICATIONS

Meier, Robert J., et al. "Simultaneous photographing of oxygen and pH in vivo using sensor films". Angewandte chemie, 2011, 123.46: 11085-11088. First published: Sep. 27, 2011.

Schreml, Stephan, et al. "2D luminescence imaging of pH in vivo". Edited and approved Dec. 27, 2010 in Proceedings of the National Academy of Sciences, Feb. 8, 2011. 201006945108.

* cited by examiner

FIG. 10

```
┌─────────── METHOD - 200 ───────────┐
```

┌─────────────────────────────────────────────┐
│ USING A RECEIVING UNIT COMBINED WITH AN ARRAY OF AT │
│ LEAST THREE SENSORS, FOR REPRESENTING THE │
│ ABSORPTION LEVELS OF THE LIGHT REFLECTED BY OR │
│ TRAVERSING THE TISSUE AT A LOCATION X IN THE TISSUE │
└─────────────────────────────────────────────┘
                    ↓  ⟍ 110

┌─────────────────────────────────────────────┐
│ GENERATING SPATIAL-TEMPORAL ELECTRONIC SIGNALS │
│ $A_3(X,T)$, $A_2(X,T)$ AND $A_1(X,T)$ RESPECTIVELY WITH THE SENSOR │
│ WAVELENGTHS L1, L2 AND L3 WHERE │
│ $0 <= A_3(X,T) <= A_2(X,T) < A_1(X,T)$ │
└─────────────────────────────────────────────┘
                    ↓  ⟍ 120

┌─────────────────────────────────────────────┐
│ USE TRANSFER FUNCTION CONNECTING ACTUAL PH │
│ VALUE OF TISSUE IN LOCATION X AT TIME T AND OUTPUT │
│ OF ORDERED FUNCTION F1 TARGETED TO SPECIFIC ORGAN │
│ OR TO BLOOD, WHEREIN F1 IS MONOTONIC AND THE │
│ TISSUE SENSED AND FOR WHICH ACTUAL PH IS TAKEN │
│ ARE OF SAME ORGAN OR BOTH BLOOD TISSUE │
└─────────────────────────────────────────────┘
                          ⟍ 130

APPARATUS AND METHOD OF GENERATING PH OF SUBJECT FROM AT LEAST THREE WAVELENGTHS

FIELD AND BACKGROUND OF THE INVENTION

The present invention is in the field of medical diagnostic devices and methods and more particularly, to provide a device, and a method of creating such a device, configured to obtain a pH level of a tissue of a mammalian subject from sensing the tissue.

The pH of a subject's tissue, such as the subject's skin, is important, among other things, because pH is an important medical diagnostic tool.

SUMMARY OF THE INVENTION

One aspect of the present invention is a method of creating a device configured to obtain a pH level of a tissue of a mammalian subject from sensing the tissue, the tissue comprising an organ or blood, the method comprising determining and recording an actual pH of the tissue of a member of a population of the mammalian subjects using a pH indicator and repeating for a plurality of members of the population; using a light source to shine light on the tissue; using an array of at least three optical sensors to absorb the light that reflects from and/or that traverses the tissue under consideration and thereby obtain at least three electronic digital signals, wherein the first electronic signal $A_1(X,t)$ represents the light absorbed by the tissue under consideration at location $X=(X,Y,Z)$ at time t and at wavelength $L_1$, the second electronic signal $A_2(X,t)$ represents the light absorbed by the tissue under consideration at location $X=(X,Y,Z)$ at time t and at wavelength $L_2$, the third electronic signal $A_3(X,t)$ represents the light absorbed by the tissue under consideration at location $X=(X,Y,Z)$ at time t and at wavelength $L_3$, and wherein a finite absorption range of the three wavelength $L_1$, $L_2$ and $L_3$ is such that $0<=A_3(X,t)<=A_2(X,t)<A_1(X,t)$; and using an electronic processing unit to receive the at least three electronic digital signals and apply an ordered function, F1, targeted to tissue of a specific organ or to blood tissue, to spatial temporal information comprising information in location X at time t of each wavelength $L_1$, $L_2$, $L_3$, wherein the ordered function, F1, is a monotone increasing or decreasing function to be used by a transfer function to present a Look Up Table connecting between actual values computed by F1 and the actual pH of the tissue under consideration in the location X at time t.

A further aspect of the present invention is a method of obtaining a pH level of a tissue of a mammalian subject from sensing the tissue, the tissue comprising an organ or blood, the method comprising using a receiving unit combined with an array of at least three sensors, for representing the absorption levels of the light reflected by or traversing the tissue under consideration of a mammalian at a location X in the tissue at time t, generating spatial-temporal electronic signals $A_3(X,t)$, $A_2(X,t)$ and $A_1(X,t)$ respectively with the sensor wavelengths L1, L2 and L3 where $0<=A_3(X,t)<=(A_2(X,t)<A_1(X,t)$; and using a transfer function of an electronic processing unit, the transfer function reflecting the connection between an actual pH value of the tissue in location X at time t and an output of an ordered function F1 targeted to a specific organ or to blood, wherein the function F1 is a monotone function, wherein the tissue sensed and the tissue for which the actual pH is taken are both of a same organ or are both blood tissue.

A still further aspect of the present invention is an apparatus configured to obtain a pH level of a tissue of a mammalian subject from sensing the tissue, the tissue comprising an organ or blood, the apparatus comprising an array of at least three optical sensors configured to absorb light shined on the tissue from a light source, the light reflecting from and/or traversing the tissue under consideration, and to thereby obtain at least three electronic digital signals, wherein the first electronic signal $A_1(X,t)$ represents the light absorbed by the tissue under consideration in location $X=(X,Y,Z)$ at time t and at wavelength $L_1$, the second electronic signal $A_2(X,t)$ represents the light absorbed by the tissue under consideration in location $X=(X,Y,Z)$ at time t and at wavelength $L_2$, the third electronic signal $A_3(X,t)$ represents the light source absorbed by the tissue under consideration in location $X=(X,Y,Z)$ at time t and at wavelength $L_3$, and wherein a finite absorption range of the three wavelength L1, L2 and $L_3$ is such that $0<=A_3(X,t)<=A_2(X,t)<A_1(X,t)$; and an electronic processing unit configured to receive the at least three electronic digital signals and to apply an ordered function, F1, targeted to a specific organ or to blood tissue, to spatial temporal information comprising information in location X at time t of each wavelength $L_1$, $L_2$, $L_3$, wherein the ordered function, F1, is a monotone increasing or decreasing function to be used by a transfer function for presentation as a Look Up Table connecting between the actual values computed by F1 and an actual pH of the tissue under consideration in the location X at time t, the actual pH previously measured by a pH indicator.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein:

FIG. 1D is a display of a skin tissue and its pH (along with other parameters) measured using a regular digital camera, in accordance with an embodiment of the present invention;

FIG. 3 is a flow chart showing a further method of the present invention.

DETAILED DESCRIPTION OF THE INVENTION

Figure 1A:
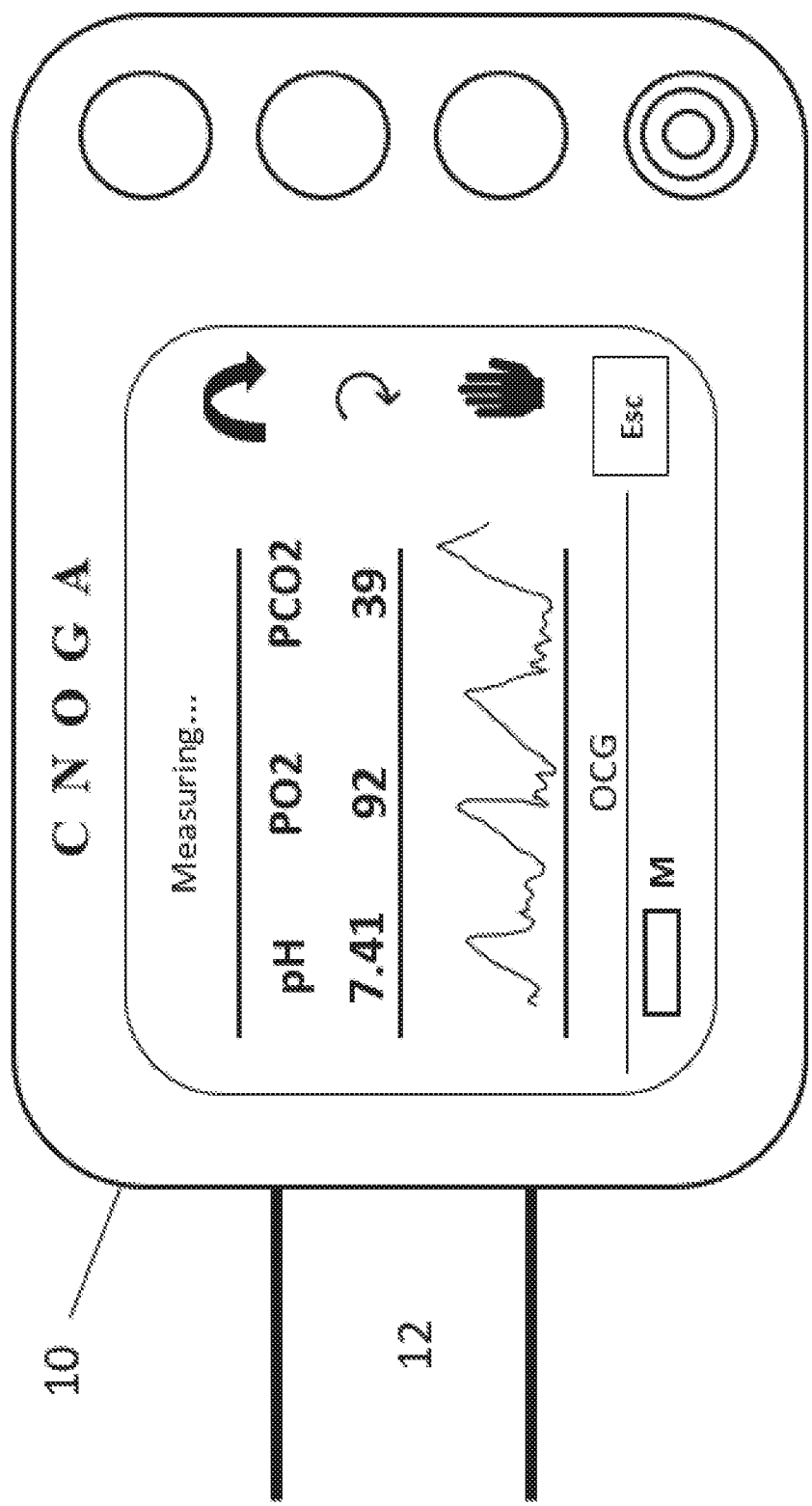
FIG. 1A is a front view of a device that measures capillary blood pH, in accordance with one embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides in certain embodiments an apparatus 10 configured to obtain a pH level of a tissue of a mammalian subject from sensing the tissue. The tissue comprises an organ (i.e. tissue of the organ) or blood. In a typical case, a subject may place their finger inside a device at a portion of the device of the present invention that is configured to receive the finger. Other embodiments may utilize an endoscope or other probe or a digital pill in order to provide the optical sensors with access to the tissue, i.e. organ or blood. In other cases, tissue of other organs of the body (besides skin) is tested, and in some other embodiments blood tissue of a mammalian subject is tested. "Tissue" as used in the invention herein is not limited to blood tissue and includes muscle tissue, fat tissue and other human tissue. For example, a probe can probe through human tissue other than through a blood vessel. Blood tissue also does not refer only to capillary blood but also includes arterial blood (which is more alkaline than capillary blood) as well as venous blood. Other methods of access that may be developed in the future are also within the invention. Accordingly, even though FIGS. 1A, 1C and 1D describe certain details of the apparatus and method in the context of measuring capillary blood pH or photographing the skin with a digital camera, the electronic processing and other aspects of the invention described herein apply equally well (unless otherwise stated) to other embodiments, such as embodiments utilizing an endoscope, digital pill and embodiments that measure organs other than the skin or blood.

Furthermore, and in general, the term "tissue" as used in the invention herein refers to live human tissue in accordance with certain embodiments and in accordance with other embodiments "tissue" as used in the invention herein refers to in vitro tissue such as a laboratory sample of dead tissue. The method of obtaining the pH is the same for dead tissue as for live tissue except for the fact that providing access to the tissue by the optical sensors is typically easier in the case of dead tissue.

The apparatus 10 may comprise an array of at least three optical sensors configured to absorb light shined on the tissue from a light source, the light reflecting from and/or traversing the tissue under consideration, and to obtain at least three electronic digital signals. In one option, the first electronic signal $A_1(X,t)$ represents the light absorbed by the tissue under consideration in location $X=(X,Y,Z)$ at time t and at wavelength $L_1$, the second electronic signal $A_2(X,t)$ represents the light absorbed by the tissue under consideration in location $X=(X,Y,Z)$ at time t and at wavelength $L_2$, and the third electronic signal $A_3(X,t)$ represents the light source absorbed by the tissue under consideration in location $X=(X,Y,Z)$ at time t and at wavelength $L_3$, and wherein a finite absorption range of the three wavelength L1, L2 and $L_3$ is such that $0<=A_3(X,t)<=A_2(X,t)<A_1(X,t)$. The apparatus in certain embodiments further comprises an electronic processing unit configured to receive the at least three electronic digital signals and to apply an ordered function, F1, targeted to a specific organ or to blood tissue, to spatial temporal information comprising information in location X at time t of each wavelength $L_1$, $L_2$, $L_3$. The ordered function, F1, in an embodiment of the present invention, is a monotone increasing or decreasing function. In certain embodiments, this monotone function, F1, is to be used by a transfer function for mapping and presentation as a Look Up Table connecting between the actual values computed by F1 and an actual pH of the tissue under consideration in the location X at time t, the actual pH previously measured by a pH indicator. "F1" is a name that has been assigned to this ordered function in certain embodiments.

Certain other embodiments of the present invention as methods are also described. One such method is a method to make the above-referenced apparatus 10 comprising determining and recording an actual pH of the tissue of a member of a population of the mammalian subjects, for example using a pH indicator that chemically detects ions and repeating for a plurality of members of the population. Other technologies may be known or later developed for recording the actual pH consistent with the present invention. The method may also comprises using a light source to shine light on the tissue (where "tissue" is (i) tissue of an organ or (ii) blood); using an array of at least three optical sensors to absorb the light that reflects from and/or that traverses the tissue under consideration and thereby obtain at least three electronic digital signals. In certain embodiments, the fast electronic signal $A_1(X,t)$ represents the light absorbed by the tissue under consideration at location $X=(X,Y,Z)$ at time t and at wavelength L1, the second electronic signal $A_2(X,t)$ represents the light absorbed by the tissue under consideration at location $X=(X,Y,Z)$ at time t and at wavelength $L_2$, the third electronic signal $A_3(X,t)$ represents the light source absorbed by the tissue under consideration at location $X=(X,Y,Z)$ at time t and at wavelength $L_3$. In certain embodiments, a finite absorption range of the three wavelength L1, L2 and $L_3$ is such that $0<=A_3(X,t)<=A_2(X,t)<A_1(X,t)$. The method may also comprises using an electronic processing unit to receive the at least three electronic digital signals and apply an ordered function, F1, targeted to tissue of a specific organ or to blood tissue, to spatial temporal information comprising information in location X at time t of each wavelength $L_1$, $L_2$, $L_3$, wherein the ordered function, F1, is a monotone increasing or decreasing function to be used by a transfer function for mapping and for presentation as a Look Up Table connecting between actual values computed by F1 and the actual pH of the tissue under consideration in the location X at time t.

Another such method is an embodiment of the invention describing a method of obtaining a pH level of a tissue of a mammalian subject from sensing the tissue, the tissue comprising an organ (i.e. tissue of the organ) or blood. The method may comprise a step of using a receiving unit combined with an array of at least three sensors, for representing the absorption levels of the light reflected by or traversing the tissue under consideration of a mammalian at a location X in the tissue. The method may further comprise a step of generating spatial-temporal electronic signals $A_3(X,t)$, $A_2(X,t)$ and $A_1(X,t)$ respectively with the sensor wavelengths L1, L2 and L3 where $0<=A_3(X,t)<=A_2(X,t)<A_1(X,t)$. the method may also comprise a step of using a transfer function reflecting the connection between an actual pH value of the tissue in location X at time t and an output of an ordered function F1 targeted to a specific organ or to blood, wherein the function F1 is a monotone function, wherein the tissue sensed and the tissue for which the actual pH is taken are both of a same organ or are both blood tissue.

The principles and operation of an Apparatus and Method of Generating pH of Subject From Sequence of Color Images may be better understood with reference to the drawings and the accompanying description.

Figure 1B:
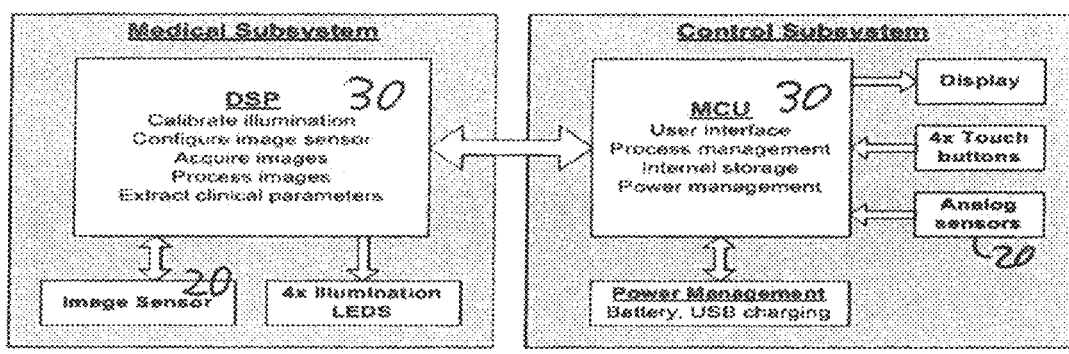
FIG. 1B is a schematic representation of sensors, hardware and software of the device of FIG. 1A, in accordance with one embodiment of the present invention.
Figure 1C:
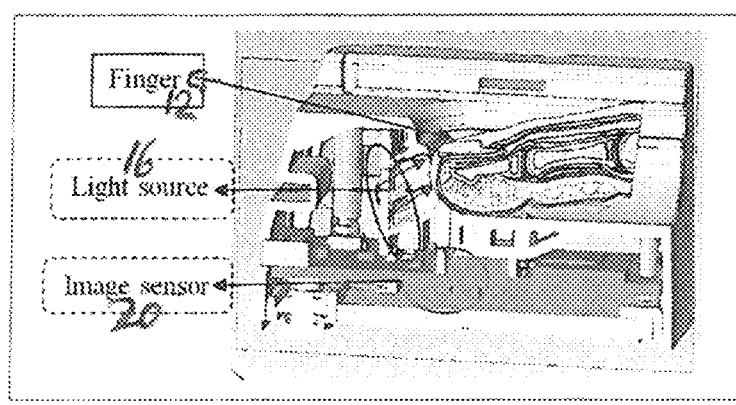
FIG. 1C is a sectional view showing the inside of a device as in FIG. 1A from the side, in accordance with one embodiment of the present invention.

As seen from FIG. 1A-FIG. 1B, the present invention, in one embodiment, is an apparatus 10 configured to obtain a pH level of a tissue of a mammalian subject from sensing the tissue, the tissue comprising an organ (such as tissue of skin, liver, etc.) or blood. In FIG. 1A, a human finger 12 has been inserted into a receiving area of apparatus 10 and the measured capillary blood pH in the capillaries of this finger shows a reading of 7.41. FIG. 1D shows a display that includes a picture of a skin tissue of a human and a number of bioparameter readings which include a reading of skin pH at 5.339 for the human by taking a picture of the human's facial skin using an ordinary digital camera. The output of the digital camera was fed into an electronic processing unit 30 of apparatus 10 for processing in accordance with an embodiment of the method and apparatus of the invention.

Apparatus 10 may comprise an array 20 of at least three optical sensors 20 configured to absorb light shined on the tissue from a light source 16 (FIG. 1C), the light reflecting from and/or traversing the tissue under consideration. In one embodiment, array 20 of at least three optical sensors is an image sensor or a plurality of image sensors, for example at least three image sensors. The array 20 of at least three optical sensors may also be configured to obtain at least three electronic digital signals, wherein the first electronic signal $A_1(X,t)$ may represent the light absorbed by the tissue under consideration in location $X=(X,Y,Z)$ at time t and at wavelength L1, the second electronic signal $A_2(X,t)$ may represent the light absorbed by the tissue under consideration in location $X=(X,Y,Z)$ at time t and at wavelength $L_2$, the third electronic signal $A_3(X,t)$ may represent the light source absorbed by the tissue under consideration in location $X=(X,Y,Z)$ at time t and at wavelength $L_3$, and wherein a finite absorption range of the three wavelength L1, L2 and $L_3$ is such that $0<=A_3(X,t)<=A_2(X,t)<A_1(X,t)$.

Apparatus 10 may also comprise any and all necessary hardware and software (for example as part of or together with electronic processing unit 30 (FIG. 1B)) for supporting the array of at least three optical sensors 20 (FIG. 1B). In one non-limiting example, the three electronic digital signals are three color digital images representing three wavelengths, wherein $A_3(X,t)=B(x,y,t)$ is considered the Blue color, wherein $A_2(x,y,t)=G(X,t)$ is considered the Green color and wherein $R(x,y,t)=A_1(X,t)$ is considered the Red color, wherein the spatial pixel location $x=\mu X/Z$, $y=\mu Y/Z$, $\mu$ is the focal constant and t is time.

As shown in FIGS. 1A-1B, electronic processing unit 30 may be configured to receive the at least three electronic digital signals and to apply an ordered function, F1, to spatial temporal information comprising information in location X at time t of each wavelength $L_1$, $L_2$, $L_3$. The ordered function, F1, in certain embodiments, is a monotone increasing or decreasing function and may be configured to be used by a transfer function for mapping and to present a Look Up Table connecting between the actual values computed by F1 and an actual pH of the tissue under consideration in the location X at time t, the actual pH previously measured by, for example, a pH indicator, for example a pH indicator that chemically detects ions.

The ordered function F1 in certain embodiments should be such that one or more of the following is true: (i) F1 locally increases whenever the actual pH increases, (ii) F1 locally decreases whenever the actual pH decreases, (iii) F1 locally increases whenever the actual pH decreases, (iv) F1 locally decreases whenever the actual pH increases. In that way, there is matching order between F1, and the range of actual pH values. Reference to the actual pH refers to the actual pH as determined for example by a pH indicator used on the tissue under consideration, for example a pH indicator that chemically detects ions.

For example, the ordered function, in one embodiment, includes one of, or a combination of one or more of, the following structures: $F1=(A_2-A_3)(A_1-A_3)-(A_1-A_2)^2$, $F1=(A_2-A_3)/(A_1-A_3)$, $F1=(A_1-A_2)/(A_1-A_3)$, $F1=(A_1/A_2)$, $F1=(A_1/A_3)$, $F1=(A_2/A_3)$, $F1=(A_2-A_3)(A_1-A_3)/(A_1-A_2)^2$, $F1=(A_2-A_3)(A_1-A_2)/(A_1-A_3)^2$, $F1=(A_2-A_3)(A_1-A_2)/(A_1-A_3)^2$, and $F1=(A_1-A_3)^2-(A_2-A_3)(A_1-A_2)$, wherein $B=A_3$, $G=A_2$ and $R=A_1$ and wherein the color values R, G and B satisfy $B<=G<R$. In another embodiment, the ordered function includes one of, or a combination of one or more of, the following structures: $F1=(A_2-A_3)(A_1-A_3)-(A_1-A_2)^2$, $F1=(A_2-A_3)/(A_1-A_3)$, $F1=(A_1-A_2)/(A_1-A_3)$, $F1=(A_2-A_3)$ $(A_1-A_3)/(A_1-A_2)^2$, $F1=(A_2-A_3)(A_1-A_2)/(A_1-A_3)^2$, $F1=(A_2-A_3)(A_1-A_2)/(A_1-A_3)^2$, and $F1=(A_1-A_3)^2-(A_2-A_3)(A_1-A_2)$, wherein $B=A_3$, $G=A_2$ and $R=A_1$ and wherein the color values R, G and B satisfy $B<=G<R$. In another embodiment, the ordered function includes one of, or a combination of two or more of, the following structures: $F1=(A_2-A_3)(A_1-A_3)-(A_1-A_2)^2$, $F1=(A_2-A_3)/(A_1-A_3)$, $F1=(A_1-A_2)/(A_1-A_3)$, wherein $B=A_3$, $G=A_2$ and $R=A_1$ and wherein the color values R, G and B satisfy $B<=G<R$. In another embodiment, the ordered function includes one of, or a combination of two or more of, the following structures: $F1=(A_2-A_3)(A_1-A_3)-(A_1-A_2)^2$, $F1=(A_2-A_3)/(A_1-A_3)$, $F1=(A_1-A_2)/(A_1-A_3)$. In another embodiment, the ordered function has the following form $F1=(A_2-A_3)(A_1-A_3)-(A_1-A_2)^2$. In another embodiment, the ordered function includes $F1=(A_2-A_3)(A_1-A_3)-(A_1-A_2)^2$, wherein $B=A_3$, $G=A_2$ and $R=A_1$ and Wherein the color values R, G and B satisfy $B<=G<R$.

In one embodiment, the ordered function, F1, includes expressions, each expression representing an interval such that the function, F1, has a golden ratio interval structure that includes a first interval that comprises a difference between two absorption levels at wavelengths $L_1$, $L_2$, a second interval that comprises a difference between absorption levels at the wavelengths $L_2$, $L_3$ and a third interval that comprises a difference between absorption levels at the wavelengths L1, and $L_3$.

The device and method of the present invention is in certain embodiments targeted to "specific tissue", i.e. blood tissue or tissue of a specific organ. For example, a device of the present invention may be calibrated for liver tissue, for example, by taking actual liver tissue pHs of the livers of a multiplicity of mammalian subjects. In another alternative, a device of the present invention is calibrated for blood, for example, by taking actual blood pHs of the blood of a multiplicity of mammalian subjects. In a further alternative, a device of the present invention is calibrated for skin pH, for example, by taking actual skin pHs of the skin tissue of a multiplicity of mammalian subjects. The number of subjects may vary with the organ or blood but is sufficient to have an average value that is reliable, according to standards used by those skilled in the art.

Figure 2:
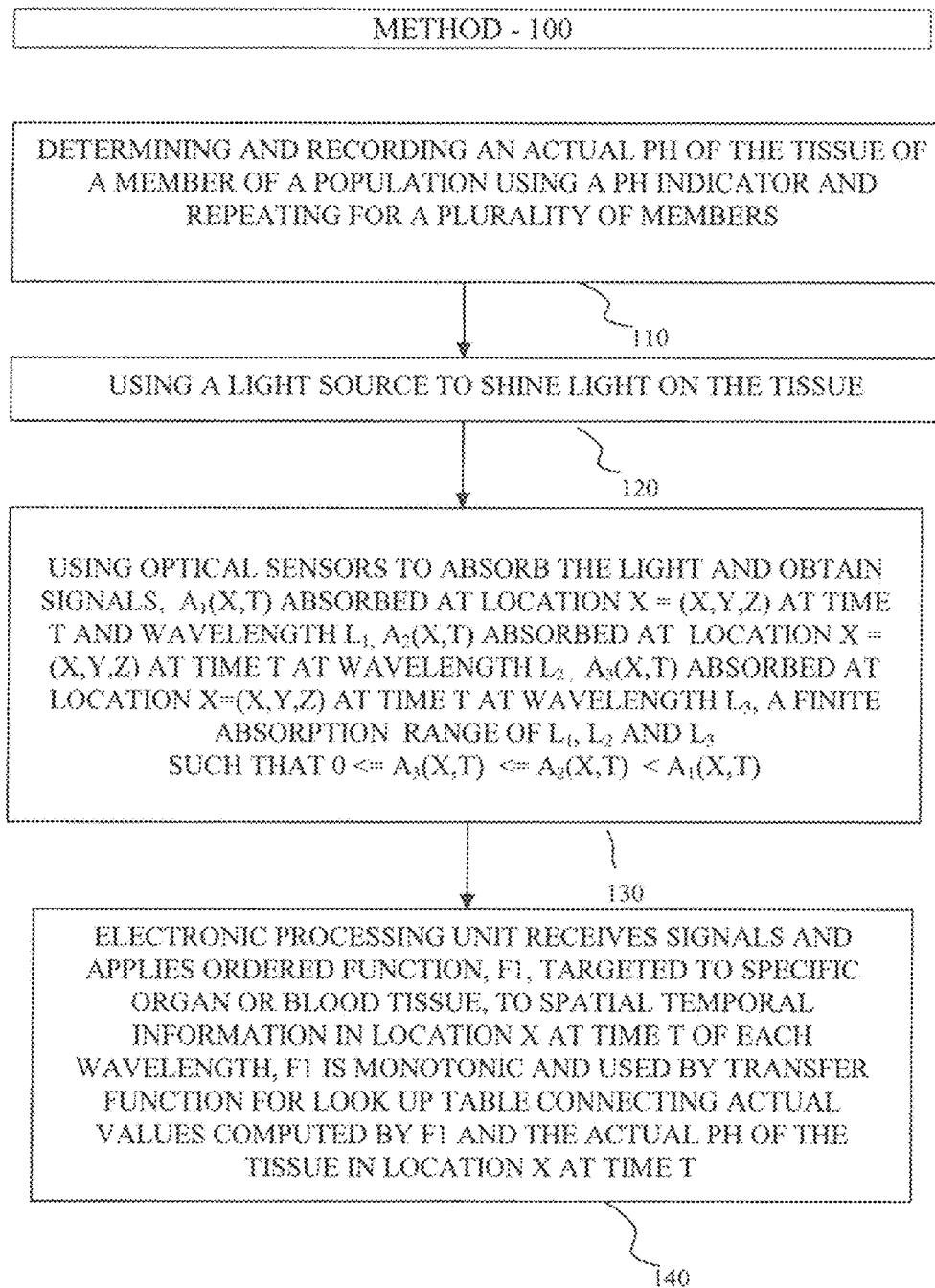
FIG. 2 is a flowchart showing a method of the present invention.

As shown in the flow chart of FIG. 2, the present invention, in one embodiment, is a method 100 of creating a device configured to obtain a pH level of a tissue of a mammalian subject from sensing the tissue, the tissue comprising an organ (i.e. tissue of the organ) or blood. Method 100 may therefore comprise a step 110 of determining and recording an actual pH of the tissue of a member of a population of the mammalian subjects, for example using a pH indicator that chemically detects ions and repeating for a plurality of members of the population. Step 120 of method 100 may further comprise using a light source to shine light on the tissue. Method 100 may also comprise a step 130 of using an array of at least three optical sensors to absorb the light that reflects from and/or that traverses the tissue under consideration and thereby obtain at least three electronic digital signals.

In regard to the at least three electronic signals of step 130, the first electronic signal $A_1(X,t)$ may represent the light absorbed by the tissue under consideration at location $X=(X,Y,Z)$ at time t and at wavelength $L_1$, the second electronic signal $A_2(X,t)$ may represent the light absorbed by the tissue under consideration at location $X=(X,Y,Z)$ at time t and at wavelength $L_2$, and the third electronic signal $A_3(X,t)$ may represent the light source absorbed by the tissue under consideration at location $X=(X,Y,Z)$ at time t and at wavelength $L_3$. In an embodiment of method 100, a finite absorption range of the three wavelength L1, L2 and $L_3$ is such that $0<=A_3(X,t)<=A_2(X,t)<A_1(X,t)$.

Method 100 may also include a step 140 of using an electronic processing unit to receive the at least three electronic digital signals and apply an ordered function, F1, targeted to tissue of a specific organ or to blood tissue, to spatial temporal information comprising information in location X at time t of each wavelength $L_1$, $L_2$, $L_3$, wherein in one embodiment the ordered function, F1, is a monotone increasing or decreasing function to be used by a transfer function to present a Look Up Table connecting between actual values computed by F1 and the actual pH of the tissue under consideration in the location X at time t.

A further step of method 100 may include setting a particular scalar value of the ordered function F1 to correspond to an ideal pH for the targeted organ or the blood. The ideal pH may take into consideration characteristics of the mammalian subject, for example factors affecting normal pH such as age and other factors.

As shown in the flow chart of FIG. 3, the present invention may also be described as a method 200 of obtaining a pH level of a tissue of a mammalian subject from sensing the tissue, the tissue comprising an organ or blood. Method 200 comprises a step 210 of using a receiving unit combined with an array of at least three sensors, for representing the absorption levels of the light reflected by or traversing the tissue under consideration of a mammalian at a location X in the tissue at time t. Method 100 may comprise a step 130 of using an array of at least three optical sensors to absorb the light that reflects from and/or that traverses the tissue under consideration and thereby obtain at least three electronic digital signals. Method 200 may also comprise a step 220 of generating spatial-temporal electronic signals $A_3(X,t)$, $A_2(X,t)$ and $A_1(X,t)$ respectively with the sensor wavelengths L1, L2 and L3 where $0<=A_3(X,t)<=(A_2(X,t)<A_1(X,t)$. Method 200 may include a step 230 of using a transfer function, of an electronic processing unit, the transfer function reflecting the connection between an actual pH value of the tissue in location X at time t and an output of an ordered function F1 targeted to a specific organ or to blood, wherein the function F1 is a monotone function, wherein the tissue sensed and the actual tissue measured, are both of a same organ or are both blood tissue. Any of the details of ordered function F1 applicable to method 100 or apparatus 10 are applicable to method 200. For example, the transfer function may connect between the values of the actual pH and the output values of the function F1.

As in method 100, in method 200 also the ordered function F1 should be such that one or more of the following is true: (i) F1 increases whenever the actual pH increases, (ii) F1 decreases whenever the actual pH decreases, (iii) F1 increases whenever the actual pH decreases, (iv) F1 decreases whenever the actual pH increases. Reference to the actual pH refers to the actual pH as determined by a pH indicator used on the tissue under consideration, for example a pH indicator that chemically detects ions.

The actual pH may be pre-calculated based on a subset of tissues of a mammalian population.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A method of creating a device configured to obtain a pH level of a tissue of a mammalian subject from sensing the tissue, the tissue comprising an organ or blood, the method comprising:

determining and recording an actual pH of the tissue of a member of a population of the mammalian subjects using a pH indicator and repeating for a plurality of members of the population;

using a light source to shine light on the tissue;

using an array of at least three optical sensors to absorb the light that reflects from and/or that traverses the tissue under consideration and thereby obtain at least three electronic digital signals, wherein the first electronic signal $A_1(X,t)$ represents the light absorbed by the tissue under consideration at location X at time t and at wavelength $L_1$, the second electronic signal $A_2(X,t)$ represents the light absorbed by the tissue under consideration at location X at time t and at wavelength L2, the third electronic signal $A_3(X,t)$ represents the light absorbed by the tissue under consideration at location X at time t and at wavelength $L_3$, and wherein a finite absorption range of the three wavelength $L_1$, $L_2$ and $L_3$ is such that $0<=A_3(X,t)<=A_2(X,t)<A_1(X,t)$; and using an electronic processing unit that comprises hardware and software to receive the at least three electronic digital signals and apply an ordered function, F1, targeted to tissue of a specific organ or to blood tissue, to spatial temporal information comprising information in location X at time t of each wavelength $L_1$, $L_2$, $L_3$, wherein the ordered function, F1, is a monotone increasing or decreasing function to be used by a transfer function to present a Look Up Table connecting between values computed by F1 and the actual pH of the tissue under consideration in the location X at time t, wherein the ordered function, F1, includes expressions, each expression representing an interval such that the function, F1, has a golden ratio interval structure that includes a first interval that comprises a difference between absorption levels at the wavelengths $L_1$, $L_2$, a second interval comprises a difference between absorption levels at the wavelengths $L_2$, $L_3$ and a third interval comprises a difference between absorption levels at the wavelengths $L_1$, and $L_3$.

2. The method of claim 1, wherein the array of at least three optical sensors is also an image sensor.

3. The method of claim 1, wherein the three electronic digital signals are three color digital images representing three wavelengths, wherein $A_3(X,t)=B(x,y,t)$ is considered the Blue color, wherein $A_2(x,y,t)=G(X,t)$ is considered the Green color and wherein $R(x,y,t)=A_1(X,t)$ is considered the Red color, wherein a spatial pixel location $x=\mu X/Z$, a spatial pixel location $y=\mu Y/Z$, $\mu$ is the focal constant and t is time.

4. The method of claim 1, wherein the ordered function includes one of, or a combination of one or more of, the following structures:

$F1=(A_2-A_3)(A_1-A_3)-(A_1-A_2)^2$,
$F1=(A_2-A_3)/(A_1-A_3)$,
$F1=(A_1-A_2)/(A_1-A_3)$,
$F1=(A_1/A_2)$,
$F1=(A_1/A_3)$,
$F1=(A_2/A_3)$,
$F1=(A_2-A_3)(A_1-A_3)/(A_1-A_2)^2$, $F1=(A_2-A_3)(A_1-A_2)/(A_1-A_3)^2$,
$F1=(A_2-A_3)(A_1-A_2)/(A_1-A_3)^2$, and
$F1=(A_1-A_3)^2-(A_2-A_3)(A_1-A_2)$,
wherein given that R, G and B represent color values, wherein $B=A_3$, $G=A_2$ and $R=A_1$ and wherein the color values R, G and B satisfy B<=G<R.

5. The method of claim 1, wherein the ordered function includes one of, or a combination of one or more of, the following structures:
$F1=(A_2-A_3)(A_1-A_3)-(A_1-A_2)^2$,
$F1=(A_2-A_3)/(A_1-A_3)$,
$F1=(A_1-A_2)/(A_1-A_3)$,
$F1=(A_2-A_3)(A_1-A_3)/(A_1-A_2)^2$,
$F1=(A_2-A_3)(A_1-A_2)/(A_1-A_3)^2$,
$F1=(A_2-A_3)(A_1-A_2)/(A_1-A_3)^2$,
$F1=(A_1-A_3)^2-(A_2-A_3)(A_1-A_2)$,
wherein given that R, G and B represent color values, wherein $B=A_3$, $G=A_2$ and $R=A_1$ and wherein the color values R, G and B satisfy B<=G<R.

6. The method of claim 1, wherein the ordered function includes one of, or a combination of two or more of, the following structures:
$F1=(A_2-A_3)(A_1-A_3)-(A_1-A_2)^2$,
$F1=(A_2-A_3)/(A_1-A_3)$,
$F1=(A_1-A_2)/(A_1-A_3)$,
wherein given that R, G and B represent color values, wherein $B=A_3$, $G=A_2$ and $R=A_1$ and wherein the color values R, G and B satisfy B<=G<R.

7. The method of claim 1, wherein the ordered function includes one of, or a combination of two or more of, the following structures:
$F1=(A_2-A_3)(A_1-A_3)-(A_1-A_2)^2$,
$F1=(A_2-A_3)/(A_1-A_3)$,
$F1=(A_1-A_2)/(A_1-A_3)$.

8. The method of claim 1, wherein the ordered function has the following form $F1=(A_2-A_3)(A_1-A_3)-(A_1-A_2)^2$.

9. The method of claim 1, wherein the ordered function includes $F1=(A_2-A_3)(A_1-A_3)-(A_1-A_2)^2$,
wherein given that R, G and B represent color values, wherein $B=A_3$, $G=A_2$ and $R=A_1$ and wherein the color values R, G and B satisfy B<=G<R.

10. The method of claim 1, wherein one or more of the following is true:
(i) F1 locally increases whenever the actual pH increases,
(ii) F1 locally decreases whenever the actual pH decreases,
(iii) F1 locally increases whenever the actual pH decreases,
(iv) F1 locally decreases whenever the actual pH increases.

11. The method of claim 1, further comprising using the array of the at least three optical sensors to absorb the light that reflects from and/or that traverses the tissue under consideration contemporaneously with determining and recording the actual pH of the tissue.

12. A method of obtaining a pH level of a tissue of a mammalian subject from sensing the tissue, the tissue comprising an organ or blood, the method comprising:
using a receiving unit combined with an array of at least three sensors, for obtaining absorption levels of light reflected by or traversing the tissue under consideration of a mammalian at a location X in the tissue at time t, generating spatial-temporal electronic signals $A_3(X,t)$, $A_2(X,t)$ and $A_1(X,t)$ respectively with the sensor wavelengths L1, L2 and L3 where $0<=A_3(X,t)<=A_2(X,t)<A_1(X,t)$; and
using a transfer function of an electronic processing unit, the electronic processing unit comprising hardware and software, the transfer function reflecting the connection between an actual pH value of the tissue at location X at time t and an output of an ordered function F1 targeted to a specific organ or to blood, wherein the function F1 is a monotone function, wherein the actual pH is taken of the specific organ or the blood, wherein the ordered function, F1, includes expressions, each expression representing an interval such that the function, F1, has a golden ratio interval structure that includes a first interval that comprises a difference between absorption levels at the wavelengths $L_1$, $L_2$, a second interval comprises a difference between absorption levels at the wavelengths $L_2$, $L_3$ and a third interval comprises a difference between absorption levels at the wavelengths $L_1$, and $L_3$.

13. A method of claim 12, where in the actual pH is pre calculated on a subset of tissues of a mammalian population.

14. A method of claim 12, wherein the transfer function connects between the values of the actual pH and the output values of the function F1.

15. An apparatus configured to obtain a pH level of a tissue of a mammalian subject from sensing the tissue, the tissue comprising an organ or blood, the apparatus comprising:
an array of at least three optical sensors configured to absorb light shined on the tissue from a light source, the light reflecting from and/or traversing the tissue under consideration, and to thereby obtain at least three electronic digital signals,
wherein the first electronic signal $A_1(X,t)$ represents the light absorbed by the tissue under consideration in location X at time t and at wavelength $L_1$, the second electronic signal $A_2(X,t)$ represents the light absorbed by the tissue under consideration in location X at time t and at wavelength $L_2$, the third electronic signal $A_3(X,t)$ represents the light source absorbed by the tissue under consideration in location X at time t and at wavelength $L_3$, and wherein a finite absorption range of the three wavelength L1, L2 and $L_3$ is such that $0<=A_3(X,t)<=A_2(X,t)<A_1(X,t)$; and
an electronic processing unit configured to receive the at least three electronic digital signals and to apply an ordered function, F1, targeted to a specific organ or to blood tissue, to spatial temporal information comprising information in location X at time t of each wavelength $L_1$, $L_2$, $L_3$, wherein the ordered function, F1, is a monotone increasing or decreasing function to be used by a transfer function for presentation as a Look Up Table connecting between the values computed by F1 and an actual pH of the tissue under consideration in the location X at time t, the actual pH previously measured by a pH indicator, wherein the ordered function, F1, includes expressions, each expression representing an interval such that the function, F1, has a golden ratio interval structure that includes a first interval that comprises a difference between absorption levels at the wavelengths $L_1$, $L_2$, a second interval comprises a difference between absorption levels at the wavelengths $L_2$, $L_3$ and a third interval comprises a difference between absorption levels at the wavelengths $L_1$, and $L_3$, the electronic processing unit comprising hardware and software.

16. The apparatus of claim 15, wherein the ordered function includes one of, or a combination of two or more of, the following structures:

$F1=(A_2-A_3)(A_1-A_3)-(A_1-A_2)^2$,
$F1=(A_2-A_3)/(A_1-A_3)$,
$F1=(A_1-A_2)/(A_1-A_3)$,
   wherein given that R, G and B represent color values, wherein $B=A_3$, $G=A_2$ and $R=A_1$ and wherein the color values R, G and B satisfy $B<=G<R$.

17. The apparatus of claim 15, wherein the ordered function F1 includes the structure $(A_2-A_3)(A_1-A_3)-(A_1-A_2)^2$.

18. The apparatus of claim 15, wherein the ordered function includes one of, or a combination of one or more of, the following structures:
$F1=(A_2-A_3)(A_1-A_3)-(A_1-A_2)^2$,
$F1=(A_2-A_3)/(A_1-A_3)$,
$F1=(A_1-A_2)/(A_1-A_3)$,
$F1=(A_1/A_2)$,
$F1=(A_1/A_3)$,
$F1=(A_2/A_3)$,
$F1=(A_2-A_3)(A_1-A_3)/(A_1-A_2)^2$,
$F1=(A_2-A_3)(A_1-A_2)/(A_1-A_3)^2$,
$F1=(A_2-A_3)(A_1-A_2)/(A_1-A_3)^2$, and
$F1=(A_1-A_3)^2-(A_2-A_3)(A_1-A_2)$,
   wherein given that R, G and B represent color values, wherein $B=A_3$, $G=A_2$ and $R=A_1$ and wherein the color values R, G and B satisfy $B<=G<R$.

\* \* \* \* \*